(12) United States Patent
Kishimoto et al.

(10) Patent No.: US 7,163,679 B1
(45) Date of Patent: Jan. 16, 2007

(54) VERSICAN AND EPITHELIAL-MESENCHYMAL INTERACTION

(75) Inventors: Jiro Kishimoto, Yokohama (JP); Robert Burgeson, Marblehead, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/565,949

(22) Filed: May 5, 2000

Related U.S. Application Data

(60) Provisional application No. 60/132,828, filed on May 6, 1999.

(51) Int. Cl.
*A01N 63/00* (2006.01)
*C12N 5/00* (2006.01)
*A01K 67/00* (2006.01)

(52) U.S. Cl. .................. 424/93.21; 435/325; 800/8
(58) Field of Classification Search .............. 536/23.1, 536/23.4, 24.1; 424/93.1; 435/325, 1.1; 800/3
See application file for complete search history.

(56) References Cited

U.S. PATENT DOCUMENTS

| 5,180,808 | A | 1/1993 | Ruoslahti ............ 530/350 |
| 5,908,867 | A | 6/1999 | Henry et al. ......... 514/693 |
| 6,689,936 | B1 * | 2/2004 | Burgeson et al. ........ 800/3 |

FOREIGN PATENT DOCUMENTS

| EP | 633 315 | 1/1995 |
| WO | WO 96 37237 | 11/1996 |
| WO | WO 99/30743 | 6/1999 |

OTHER PUBLICATIONS

GenBank Accession No. NT 00654, 2002.*
GenBank Accession No. UI 5963, 2002.*
Ebert et al.; A Moloney MLV-Rat Somatotropin Fusion Gene Produces Biologically Active Somatotropin in a Transgenic Pig, 1988, Molecular Endocrinology 2: 277-283.*
Mullins et al.; Perspectives Series: Molecular Medicine in Genetically Engineered Animals, 1996, J. Clin. Invest.: 1557-1560.*
Wall et. al.; Transgenic Dairy Cattle: Genetic Engineering on a Large Scale , 1997, J Dairy Sci. 80: 2213-2224.*
Hammer et.al.; Genetic Engineering Of Mammalian Embryos, 1986, J. Anim. sci. 63: 269-278.*
Moreadith et al.; Gene targeting in embryonic stem cells: the new physiology and metabolism, 1997, J. Moi. Med. 75: 208-216.*
Seamark; Progress and Emerging Problems in Livestock Transgenesis: a Summary Perspective, 1994, Reprod. Fertil. Dev. 6: 653-657.*
Chalfie et al., "Green Fluorescent Protein as a Marker for Gene Expression", Science, vol. 26, Feb. 11, 1994:802-805.

Kishimoto et al., "Human Versican Promoter-Driven Lacz . . . ", J. Investigative Dermatology, vol. 110, No. 4, Apr. 1998:151.
Kishimoto et al., "Versican Promoter Transactivation in Dermal Papilla . . . ", J. Investigative Dermatology, vol. 112, No. 4, Apr. 1999:678.
Kishimoto et al., "Selective activation of the versican . . . ", Proc. Natl. Acad. Sci. USA, vol. 96, Jun. 1999:7336-7341.
Kishimoto et al., "Developmental Study of Human Versican . . . ", Glycosaminoglycans and Proteoglycans, vol. 8, No. Supplement, p. 394A; 2292.
Naso et al., "Characterization of the Complete Genomic Structure of the Human . . . ", J. Biological Chemistry, vol. 269, No. 52, Dec. 30, 1994:32999-33008.
Zimmermann et al., "Versican Is Expressed in the Proliferating Zone . . . ", J. Cell Biology, vol. 124, No. 5, Mar. 1994:817-825.
Du Cros et al., "Association of Versican with Dermal Matrices . . . ", 1995, J.Invest. Derm. 105(3);426-431.
Kishimoto et al., "Human Versican Promoter-Driven Lacz Activity . . . ", 1998, J. Derm. Sci. 16(suppl. 1);S26.
Rhode et al., "The retinoblastoma protein modulates expression . . . ", 1996, Oncogene 12(11);2393-2401.
Cachon-Gonzalez et al. "*Structure and Expression of the Hairless Gene of Mice*", Proc. Natl. Acad. Sci., USA, vol. 91, pp. 7717-7721 (1994).
Mohan J. Investigative Dermatology, vol. 106, p. 906, abstract 605, 1996.
Davis et al., *A Nuclear GFP That Marks Nuclei in Living Drosophila Embroys; Maternal Supply Overcomes a Delay in the Appearance of Zygotic Fluorescence*, Develop. Biol., 170:726-729 (1995).
Mullins, *Molecular Medicine in Genetically Engineered Animals*, J. Clin. Invest., vol. 98, pp. S37-S40), 1996.
Mullins et al., *Expression of the DBA/2J ren-2 gene in the adrenal gland of transgemic mice*, 1989, The EMBO Journal, vol. 8, pp. 4065,4072.
Mullins et al., *Fulminant hypertension in transgenic rats harbouring the mouse Ren-2 gene*, 1990, Nature, vol. 344, pp. 541-544.
Hammer et al., *Spontaneous inflammatory disease in transgemic rats expressing HLA-B27 and Human B2m: An animal model of HLA-B27-associtaed human disorders*, 1990, Cell, vol. 63, pp. 1099-1112.
Taurog et al., *HLA-B27 in inbred and non-inbred transgenic mice: Cell surface expression and recognition as an alloantigen in the absence of human B2-microglobulin*, 1988, The Journal of Immunology, vol. 141, pp. 4020-4023.
Okabe et al., '*Green mice' as a source of ubiquitous green cells*, 1997, FERS Letters, vol. 407, pp. 313-319.
Gille Jens et al, "*Transforming growth factor—alpha—induced transcriptional activation of the vascular permeability factor (VPF/ FEGF) gene requires AP-2-dependent DNA binding and transactivation*", EMBO (European Molecular Biology Organization) Journal, vol. 16, No. 4, 1997, pp. 750-759, XP002164519.
Ramirez, A. et al., "*A 5'-upstream region of a bovine keratin 6 gene confers tissue-specific expression and hyperproliferation-related induction in transgenic mice*," Proceedings of the National Academy of Sciences of the United States of America, vol. 92, May 1995, pp. 4783-4787, XP002156382.

(Continued)

*Primary Examiner*—Joseph Woitach
(74) *Attorney, Agent, or Firm*—Fish & Richardson P.C.

(57) ABSTRACT

The invention describes versican activation and modulation of hair growth, e.g., versican expressing dermal papilla cells exhibit hair induction ability.

13 Claims, 1 Drawing Sheet

OTHER PUBLICATIONS

Bernstein, E.F. et al., "*Evaluation of sunscreens with various sun protection factors in a new transgenic mouse model of cutaneous photoaging that measure elastin promoter activation*", Journal of the American Academy of Dermatology, US, C.V. Mosby, St. Louis, MO, vol. 37, No. 5, Part 01, Nov. 1997, pp. 725-729, XP002117296.

Ikawa, M. et al., "*Green fluorescent protein as a marker in transgenic mice*" Development of growth and differentiation, JP, Japanese Society of Developmental Biologists, vol. 37, Aug. 1, 1995, pp. 455-459, XP002086829.

Damak et al. "*Expression of Human Neutrophil Elastase Gene in the Lungs of Transgenic Mice*", J. Cellular & Biochemistry Supp., Abstract V102; Apr. 3, 1992.

Himelstein et al., Oncogene 14(16): 1995-1998 (1997).

Kemp et al. "*The Glycosylation of Alpha-1 Antitrypsin in Transgenic Mice*", Animal Cell Technology: Basic: Applied Aspects, 8th Annual Conference, edited by Funatsu et al., the Netherlands: Kluwer Academic Publishers 8:517-522 (1997).

Rice et al., *Detection of Gelatinase B Expression Reveals Osteoclastic Bone Resorpotion as a Feature of Early Calvarial Bone Development*, Bone, 21(6):479-486 (Dec. 1997).

Simon et al., *Suppressor and Activator Functions Mediated by a Repeated Heptad Sequence in the Liver Fatty Acid-binding Protein Gene (Fabpl)*, J. of Biological Chemistry, 272(16):10651-10663 (Apr. 18, 1997).

Yoshizaki et al., *Increased Expression of Membrane Type 1-Matrix Metalloproteinase in Head and Neck Carcinoma*, Cancer, 79(1):139-144.

Zhang et al., *An Enhanced Green Fluorescent Protein Allows Sensitive Detection of Gene Transfer in Mammalian Cells*, Biochem. Biophys. Res. Commun., 227:707-711 (1996).

Mistelli & Spector, *Applications of the green fluorescent protein in cell biology and biotechnology*, Nat. Biotechnol., 15:961-964 (1997).

Chiocchetti et al., *Green fluorescent protein as a reporter of gene expression in transgenic mice*, Biochem. Biophys. Act., 1352:193-202 (1997).

Zhuo et al., *Live Astrocytes Visualized by Green Fluorescent Protein in Transgenic Mice*, Dev. Biology, 187:36-42 (1997).

Detmar et al., *Molecular Regulation of Angiogenesis in the Skin*, J. Invest. Dermatol., 106:207-208 (1996).

Brown, et al., *Expression of Vascular Permeability Factor (Vascular Endothelial Growth Factor) by Epidermal Keratinocytes during Wound Healing*, J. Exp. Med., 176:1375-1379 (1992).

Larcher et al., *Up-Regulation of Vascular Endothelial Growth Factor/Vascular Permeability Factor in Mouse Skin Carcinogenesis Correlates with Malignant Progression State and Activated H-ras Expression Levels*, Cancer Res., 56:5391-5396 (1996).

Bernstein et al., *Differential Expression of the Versican and Decorin Genes in Photaged and Sun-Protected Skin*, Laboratory Investigation, 72:662-669 (1995).

Huhtala et al., *Complete Structure of the Human Gene for 92-kDa Type IV Collagenase*, The Journal of Biological Chemistry, 266:16485-16490 (1991).

Itano et al., *Molecular Cloning of Human Hyaluronan Synthase*, Biochemical and Biophysical Research Communications, 222:816-820 (1996).

Mauch et al., *Role of the extracellular matrix in the degradation of connective tissue*, Arch. Dermatol. Res., 287:107-114 (1994).

Spicer et al., *Molecular Cloning and Characterization of a cDNA Encoding the Third Putative Mammalian Hyaluronan Synthase*, The Journal of Bioligical Chemistry, 272:8957-8961 (1997).

Takahashi et al., *Structure of the Human Neutrophil Elastase Gene*, The Journal of Biological Chemistry, 263:14739-14747 (1988).

Tischer et al., *The Human Gene for Vascular Endothelial Growth Factor*, The Journal of Biological Chemistry, 266:11947-11954 (1991).

Watanabe et al., *Molecular Identification of a Putative Human Hyaluronan Synthase*, The Journal of Biological Chemistry, 271:22945-22948 (1996).

Hsu-Wong et al., *Tissue-specific and Developmentally Regulated Expression of Human Elastin Promoter Activity in Transgenic Mice*, The Journal of Biological Chemistry, 269:18072-18075 (1994).

Bernstein et al., *8-Methoxypsoralen and Ultraviolet A Radiation Activate the Human Elastin Promoter in Transgenic Mice: In vivo and in vitro Evidence for Gene Induction*, Photochemistry and Photobiology, 64:369-374 (1996).

Overbeek, *Factors affecting transgenic animal production*, Transgenic animal technology, pp. 96-98, 1994.

\* cited by examiner

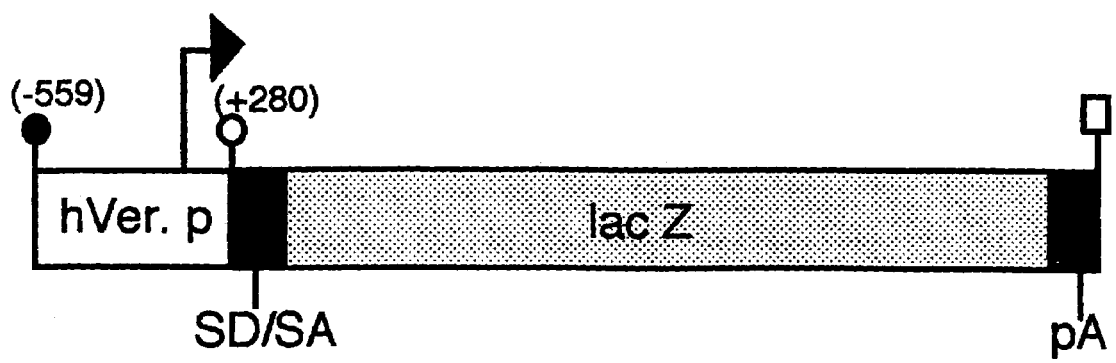

VERSICAN AND EPITHELIAL-MESENCHYMAL INTERACTION

This application claims the benefit of a previously filed Provisional Application No. 60/132,828, filed May 6, 1999, the contents of which is incorporated in its entirety.

BACKGROUND OF THE INVENTION

The invention relates generally to interactions between epithelium and mesenchyme, e.g., interactions at hair follicles, and to the processes of hair development and hair cycling.

Epithelial-mesenchymal interactions during development are essential for the induction of organogenesis for many tissues (e.g., kidney, gut, respiratory organ, cutaneous appendage). Among these, the hair follicle provides an excellent model for studying epithelial-mesenchymal interactions because: 1) it is located on the outermost layer of the body, allowing easy access and observation; 2) it has distinct epithelial and mesenchymal components; and 3) a definitive functional assay for in vivo hair induction already exists. (Weinberg, W. C., Goodman, L. V., George, C., Morgan, D. L., Ledbetter, S., Yuspa, S. H. & Lichti, U. (1993) *J. Invest. Dermatol.* 100, 229–236).

The dermal papilla (DP) is located at the bottom of the hair follicle and is the major mesenchymal component. The DP originates from condensed mesenchymal cells that lie beneath the epithelial hair germ cells (placode) in embryonic skin. These specialized mesenchymal cells are believed to be the source of the dermal-derived signaling molecule(s) involved in hair development and embryogenesis and later in postnatal hair cycling. (Hardy, M. H. (1992) *Trends Genet.* 8, 55–61).

Hair development during embryogenesis requires a series of reciprocal interactions between the epithelium and the underlying mesenchymal cells. Initially, the dermal mesenchyme signals the epithelium to form the epidermal placode. In response, the epithelium sends a message to the underlying mesenchyme to initiate mesenchymal condensation. The condensed mesenchyme then sends a message back to the epithelium promoting hair elongation. (Messenger, A. G. (1993) *J. Invest. Dermatol.* 101, 4S–9S).

There is a need in the art to investigate target gene(s) or mesenchymal-derived signaling molecules that have an active role in the dermal condensation and hair growth induction.

SUMMARY OF THE INVENTION

The invention is based, in part, on the discovery that versican-expressing cells, e.g., versican-expressing dermal papilla (DP) cells have hair-induction ability. Versican gene is a specific marker for hair inducibility and for the ability to promote aggregation and condensation of DP cells. The activity of versican gene can be used to identify or select cells e.g., DP cells, e.g., cultured DP cells, useful for testing treatments for the ability to modulate hair-induction and/or hair growth process. In addition, the promoter of the versican gene can be used for hair follicle, e.g., DP-specific expression.

In general, the invention features, a method of evaluating a cell, e.g., a DP cell or a cultured DP cell. The method can be used to evaluate the ability of a DP cell to promote aggregation or condensation, the ability of a DP cell to modulate, e.g., to promote, a mesenchymal interaction, or to modulate e.g., to promote, hair growth or induction. The method includes: providing a cell; and evaluating the expression of a versican promoter in the cell, thereby evaluating the cell.

In a preferred embodiment the cell, e.g., a DP cell, e.g., a cultured DP cell, is used to evaluate or screen a treatment for the ability to modulate hair induction or growth.

In a preferred embodiment the versican promoter is linked to a nucleic acid sequence which encodes a reporter molecule, e.g., a luminescent or fluorescent product, e.g., green fluorescent protein (GFP)

In a preferred embodiment the cells are subsequently implanted in an animal to evaluate their potential, e.g., their potential for inducing hair growth. The cells can be combined with epithelial cells, epithelial hair germ cells or placode, epithelial cell extract, or a fraction of epithelial cell extract, e.g., cytoplasmic fraction, membrane fraction, or soluble fraction and implanted in an animal.

In a preferred embodiment, a versican gene promoter is a nucleotide fragment containing about 900 bp. In a more preferred embodiment, the versican gene promoter fragment includes a nucleotide sequence upstream and/or downstream of a transcription start site, e.g., from position −559 to +280 of versican gene while the major transcription start site is position +1.

In a preferred embodiment, a cell is a mesenchymal cell, e.g., a condensed mesenchymal cell, a DP cell, a versican expressing-mesenchymal cell, a DP versican-expressing cell, or a cell selected for versican promoter activity. In another preferred embodiment, a cell is a cultured cell, e.g., cultured DP cell.

In a preferred embodiment the method further includes purifying a versican expressing cell from a cell, preferably of the same type, which does not express the versican promoter.

In another aspect, the invention features, a method of identifying a treatment capable of modulating hair growth or induction, or capable of modulating an epithelial-mesenchymal interaction or DP aggregation or condensation. The method includes providing a treatment to a cell, e.g., a DP cell or a cultured DP cell, having versican gene expression, or selected for versican promoter activity. The method can further include monitoring hair growth or induction, e.g., monitoring hair formation.

In a preferred embodiment the versican promoter is linked to a nucleic acid sequence which encodes a reporter molecule, e.g., a luminescent or fluorescent product, e.g., green fluorescent protein (GFP)

In a preferred embodiment, a versican gene promoter is a nucleotide fragment containing about 900 bp. In a more preferred embodiment, the versican gene promoter fragment includes a nucleotide sequence upstream and/or downstream of a transcription start site, e.g., from position −559 to +280 of versican gene while the major transcription start site is position +1.

In a preferred embodiment, a treated cell is a mesenchymal cell, e.g., a condensed mesenchymal cell, a DP cell, a versican expressing-mesenchymal cell, a DP versican-expressing cell, or a cell selected for versican promoter activity. In another preferred embodiment, a treated cell is a cultured cell, e.g., cultured DP cell.

In a preferred embodiment the method further includes purifying a versican expressing cell from a cell, preferably of the same type, which does not express the versican promoter.

In another aspect, the invention features, a method of identifying a treatment, e.g., a treatment that modulates versican gene, or versican promoter-dependent, expression. Modulation of versican gene, or versican promoter-dependent, expression can be predictive of the modulation of an epithelial-mesenchymal interaction or DP aggregation or condensation, and/or the modulation of hair induction and/or hair growth.

The method includes providing a treatment to a cell and monitoring versican gene or promoter activity. Modulation of versican gene or promoter activity can be predictive of the ability to modulate an epithelial-mesenchymal interaction or DP aggregation or condensation or modulate hair induction or growth, e.g., a change of versican gene or promoter activity in the treated cell but not in a control cell identifies such a treatment.

Versican gene or promoter activity can be monitored by any suitable means, e.g., measuring the level of transcription or translation of versican gene or a product under the control of a versican promoter, or the level of activity of versican gene promoter.

In a preferred embodiment, a versican gene promoter is a nucleotide fragment containing about 900 bp. In a more preferred embodiment, the versican gene promoter fragment includes a nucleotide sequence upstream and/or downstream of a transcription start site, e.g., from position −559 to +280 of versican gene while the major transcription start site is position +1.

In a preferred embodiment, a treated cell is a mesenchymal cell, e.g., a condensed mesenchymal cell, a DP cell, a versican expressing-mesenchymal cell, a DP versican-expressing cell, or a cell selected for versican promoter activity. In another preferred embodiment, a treated cell is a cultured cell, e.g., cultured DP cell.

In still another preferred embodiment, the treatment is administered in the presence of epithelial cells, epithelial hair germ cells or placode, epithelial cell extract, or a fraction of epithelial cell extract, e.g., cytoplasmic fraction, membrane fraction, or soluble fraction. A population of epithelial cells, e.g., keratinocytes or a sufficient amount of epithelial cell extract can be incubated or in contact with the to be treated cells before, during, or after the treatment, or in combination thereof.

In a preferred embodiment the treated cells are implanted in an animal to evaluate their potential, e.g., their potential for inducing hair growth. The treated cells can be combined with epithelial cells, epithelial hair germ cells or placode, epithelial cell extract, or a fraction of epithelial cell extract, e.g., cytoplasmic fraction, membrane fraction, or soluble fraction and implanted in an animal.

In another aspect, the invention features a method of inducing hair growth. The method includes introducing a first population of cells containing versican expressing cells or cells selected for versican promoter activity, e.g., DP versican expressing cells into a subject.

In a preferred embodiment, a second population of cells, e.g., containing epithelial cells, are introduced before, after, or concurrently with the introduction of the first population of cells into a subject.

In yet another aspect, the invention features, a transgenic mammal which contains a promoter of versican gene operably linked to a nucleotide sequence encoding a reporter sequence; wherein the promoter is active in dermal papilla cells of the transgenic mammal.

In a preferred embodiment, a versican promoter is capable of providing tissue and/or cell specific activity, e.g., specific activity in hair follicles. In another preferred embodiment, a versican promoter directs or drives specific promoter activity in mesenchymal cells, e.g., condensed mesenchymal cells and dermal papilla cells. In the most preferred embodiment, the versican gene promoter fragment includes a nucleotide sequence from position −559 to +280 of versican gene while the major transcription start-site is position +1.

The invention also features a method of providing dermal papilla-specific expression. The method includes providing a polynucleotide sequence which includes a versican promoter or a functional fragment or analog thereof, operably linked to a desired nucleic acid sequence; wherein the promoter is active in dermal papilla cells, e.g., specifically activated in dermal papilla cells.

In a preferred embodiment, the polynucleotide sequence encodes a growth factor, e.g., FGF-2(βFGF), FGF-7(KGF), EGF, IGF-1, NGF, TGF-β1, TGF-β2, TGF-β3, HGF, a growth factor receptor, e.g., NGFR, PDGFR, TGF-βIR, TGF-βIIr, a hormone receptor, e.g., androgen receptor, retinoic acid receptor, a morphogen molecule, e.g., BMP-2, BMP-4, epimorphin, an adhesion molecule, e.g., collagen, hyaronic acid receptor, syndecan-1, veriscan, a protease, e.g., nexin-1, or a transcription factor, e.g., LEFi, Gli1, Gli2, Gli3.

In another preferred embodiment, the polynucleotide sequence encodes a gene expressed in early hair follicle development, e.g., a homeobox gene, e.g., HoxC8, HOXD9, HoxD11, HoxD13, Msx-1, Msx-2; a transcription factor, e.g., Lef1, Whn, Id 1–3, Id 4, M-Twist; a signaling or adhesion molecules, e.g., Amphiregulin, BRCA-1, BMP-2A, BMP-4, BMP-3, BMP-7, E-Caderin, P-Caderin, Clusterin/TRPM-2, α1 Connexin, α2 Connexin, CD44, I-CAM, Epimorphin, AGFR, FGF-1 (αFGF), FGF-2 (βFGF), GFG-7 (KGF), FGFR1, FGFR2, KGFR, Hedgehog, Patched, IGF-1, c-Met, Midkine, NGF, NGFR, Pleiotrophin, PDGF-A, PDGF-B, PGGFRa, PDGFru, TGF-β1, TGF-β2, TGF-β3, TGF-BIR, TGF-BIIR, Serrate, Notch, p5.3, Neurotrophins; a retinoic acid receptor, e.g., RAR α, RAR γ; or an extracellular matrix and proteoglycan, e.g., Collagen I, III, and V, Collagen IV, and VII, Hyaluronic acid receptor, Syndecan-1, Tenascin, Perlecan, C-S-PG.

Still another feature of the invention is a method of separating a first population of cells from a second population of cells. The method includes providing a mixture of a first population of cells containing a luminescent or fluorescent product and a second population of cells which lack the luminescent or fluorescent product, and separating the first population of cells from the second population of cells, e.g., by virtue of luminescence or fluorescence.

In a preferred embodiment, a cell in the first (or both) populations is one into which a nucleotide sequence encoding a luminescent or fluorescent protein or polypeptide has been inserted.

In a preferred embodiment a cell in the first population is one into which a luminescent or fluorescent protein has been introduced, e.g., by injection or electroporation.

In a preferred embodiment a cell having a luminescent or fluorescent product is: a cell into which a nucleic acid encoding a luminescent or fluorescent product, e.g., GFP, has been introduced; a cell into which a nucleic acid encoding a promoter, not normally coupled to a luminescent or fluorescent product is coupled to a nucleic acid encoding a luminescent or fluorescent product, e.g., a skin specific or a DP cell specific promoter, e.g., a versican promoter coupled to the nucleic acid encoding a luminescent or fluorescent product, e.g., GFP.

In a particularly preferred embodiment a nucleic acid encoding a promoter coupled to a luminescent or fluorescent product has been introduced into cells of both populations but is expressed only in the first population.

In another preferred embodiment, a cell of one or both populations includes a nucleic acid sequence encoding a luminescent or fluorescent product fused to a sequence which is capable of targeting the product to a particular cell destination, e.g., to the nucleus, cytoplasm, or a membrane, e.g., the plasma membrane.

In still another preferred embodiment, a luminescent or fluorescent product, e.g., GFP is, conjugated, coupled, or attached to a partial or full-length membrane protein or a targeting sequence which, e.g., results in incorporation into the plasma membrane.

Separating a population of cells containing a fluorescent product from a population of cells that do not contain a fluorescent product can be achieved by various means, e.g., a cell sorter, a high-speed cell sorter, or a Moflo high-speed cell sorter.

The invention also features a method of modulating an epithelial-mesenchymal interaction, DP aggregation or condensation, or hair growth or induction. The method includes administering an effective amount of a treatment to a mammal in need of such treatment; the treatment modulates the level of versican in the mammal, e.g., in DP cells.

In a preferred embodiment, the modulation is promotion and an effective amount of partial or full-length versican protein, partial or full-length versican gene is administered. In a preferred embodiment the modulation is inhibition and an antibody which specifically binds to one or more versican epitopes, or a versican antisense oligo is administered.

In another aspect, the invention features, a population of cells, e.g., DP cells, e.g., cultured DP cells, which have versican promoter activity.

In a preferred embodiment, the cells have been separated from cells which do not express the versican promoter, e.g., the population is a population of DP cells, e.g., cultured DP cells, which has been separated from other DP cells, e.g., other cultured DP cells which lack versican promoter expressions.

In a preferred embodiment the cells are from a transgene animal, e.g., a mouse. The transgene animal can include a luminescent or fluorescent product coupled to a versican promoter.

In a preferred embodiment, the cells are a population of versican-expressing DP cells or a population of DP cells having a fluorescent product inside the cells.

In a particularly preferred embodiment a nucleic acid encoding a promoter coupled to a luminescent or fluorescent product has been introduced into cells of both populations but is expressed only in the first population.

A treatment, as used herein, can be an exposure to an environment, to a material, or a combination of both, e.g., contacting the cell with a compound, a small molecule, a polynucleotide, a polypeptide, a composition, or exposing the cell to a physical or chemical condition including heat-shock, freezing, and laser treatment.

A versican promoter, as used herein, is a nucleotide fragment capable of providing promoter activity, e.g., a fragment containing the nucleotide sequence upstream and/or downstream of a transcription start-site, e.g., position +1.

Modulation, as used herein, refers to promotion or inhibition.

Introducing a cell population to a subject refers to any means grafting a cell population to a suitable or desired area in a subject, e.g., fixing, contacting, implanting, exposing, or incubating a cell population to an area. A suitable or desired area for introducing a population of cells includes but not limited to skin, an area adjoining, contacting, or accessible to epithelial cells, e.g., epithelial hair germ cells, placode, or keratinocytes.

A cell population contains, e.g., contains substantially desired cells, e.g., epithelial cells or versican expressing cells means that at least 10% of the cells in the cell population are desired cells, preferably 20%, 50%, 70%, and most preferably 90% of the cells in the cell population are desired cells.

A reporter sequence as used herein, is a polynucleotide which encodes a product capable of providing a detectable signal to indicate the activity of the promoter which is operably linked to the reporter sequence. Preferred reporter sequences are those which encode products which can luminesce or fluoresce.

A particularly suitable reporter is green fluorescent protein. Modified variants of green fluorescent protein, e.g., EGFP, EBFP, EYFP, d2EGFP, ECFP, GFPuv are included within the term green fluorescent protein. EGFP is particularly preferred. These variants of GFP are commercially available by ClONTECH, Laboratories, Inc. Palo Alto, Calif. Furthermore, GFP and variants thereof, are provided in the following references, all of which are incorporated by reference: Chalfie, M. et al. (1994) Science 263:802–805; Prasher, D. C., et al. (1992) Gene 111:229–233; Inouye, S. & Tsuji, F. I. (1994) FEBS Letters 341:277–280; Wang, S. & Hazelrigg, T. (1994) Nature 369:400–403; Cody, C. W., et al. (1993) Biochemistry 32:1212–1218; Inouye, S. & Tsuji, F. I. (1994) FEBS Letters 351:211–214; Heim, R., et al. (1994) Proc. Natl. Acad. Sci, USA 91:12501–12504; Yang, T. T., et al. (1996) Nucleic Acids Res. 24(22):4592–4593; Cormack, B. P., et al. (1996) Gene 173:33–38; Crameri, A., et al. (1996) Nature Biotechnol. 14:315–319; Haas, J. et al., (1996) Curr. Biol. 6:315–324; Galbraith, D. W., et al. (1995) Methods Cell Biol. 50:1–12; Living Colors Destabilized EGFP Vectors (April 1998) CLONTECHniques XIII(2): 16–17; Living Colors pEBFP Vector (April 1997) CLONTECHniques XII(2):16–17; Heim, R. & Tsien, R. Y. (1996) Curr. Biol. 6:178–182; Ormö, et al. (1996) Science 273: 1392–1395; Mitra, R. D., et al. (1996) Gene 173:13–17.

A reporter sequence can be, a nucleotide sequence encoding a reporter gene, a sequence tag, or a chemically modified sequence activable by absorbing or releasing energy. In a preferred embodiment, a reporter sequence is a reporter gene encoding a heterologous protein, preferably a fluorescent protein or a enzymatic substrate.

A versican expressing cell refers to a cell containing an active versican gene, e.g., transcription or translation of versican gene is at a level that is at least technically detectable. In a preferred embodiment, a versican expressing cell contains a detectable amount of partial or full-length versican mRNA or protein. In another preferred embodiment, a versican expressing cell contains a significant amount of full-length versican mRNA or protein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is the construction of versican-lacZ transgene. The number in parenthesis indicates the human versican sequence position from the major transcription site as +1 (arrow). Synthetic splice donor and acceptor sites are labeled SD/SA; polyadenylation signal sequence is labeled pA. The black circle denotes EcoRI; open circle denotes XhoI; rectangular box denotes XbaI.

DETAILED DESCRIPTION

The invention is further described in the following examples, which do not limit the scope of the invention described in the claims.

In the following examples we demonstrate that a short fragment of the versican promoter is sufficient to drive mesenchymal condensation and DP-specific gene expression during hair development. This versican gene expression correlates with the in vivo hair inductive ability of isolated DP-derived cells. Therefore, versican is the first characterized dermal papilla-specific gene marker for hair inductivity.

Generation of Transgenic Mice

The 839 bp fragment of the functional human versican promoter (−559 to +280) (Naso, M. F., Zimmermann, D. R. & Iozzo, R. V. (1994) *J. Biol. Chem.* 269, 32999–33008) was obtained from human genomic DNA. This fragment contains the functional promoter region (−559 to +1) and the first untranslated exon that is not interrupted by an intron. The fragment was inserted in front of the lacZ (β-galactosidase) reporter gene in the PNASS2β vector (Clontech, San Francisco, Calif.). Transgene DNA for pronuclear injection was excised as an EcoRI-XbaI, 4732 bp fragment (FIG. 1). The linearized construct was injected into fertilized oocytes of DBA2xC57BL6 (DBF1) mice, and the eggs were implanted into pseudo-pregnant foster mothers. The offspring (F0) were tested for chromosomal integration of the transgene by Southern hybridization or PCR. All transgenic analyses were performed on F1–F3 hemizygous offspring. For the GFP reporter transgenic mouse, lacZ was replaced by the EGFP (Enhanced GFP) gene fragment (Clontech, San Francisco, Calif.) in the same transgene cassette.

β-Galactosidase Histochemistry

Collected transgenic mouse embryos (from embryonic day [E]13.5, E14.5, E15.5 and E17.5) were fixed with 0.5% glutaraldehyde in PBS for 30 min to 12 hr, depending on the embryonic stage. Embryos at E15.5 and E17.5 were cut in half for easy substrate penetration into the skin. The histochemical staining procedure for β-galactosidase activity was followed as described previously using X-gal as a substrate (Kawabe, T. T., Rea, T. J., Flenniken, A. M., Williams, B. R., Groppi, V. E. & Buhl, A. E. (1991) *Development* 111, 877–879). Sections were either directly mounted or counterstained with eosin after dewaxing. For postnatal skin tissue, 5 mm strips of back skin were fixed for 15 min, and subjected to the same procedure. Sections were then counterstained with eosin.

In situ Hybridization

For in situ hybridization, transgenic embryo (E13.5) or newborn skin was fixed in freshly prepared 4% paraformaldehyde, and processed through a standard paraffin embedding protocol under RNase-free conditions. Digoxigenin-labeled in situ hybridization was performed on 8 μm paraffin sections, as described previously (Kishimoto, J., Cox, H., Keverne, E. B. & Emson, P. C. (1994) *Mol. Brain. Res.* 23, 33–39). cDNA for lacZ and mouse versican (nucleotides 243–880, corresponding to a portion of the hyaluronan-binding domain that detects all versican isoforms [8]) were amplified by RT-PCR. Digoxigenin-labeled antisense and sense RNA probes were prepared by in vitro transcription with T7 RNA polymerase using these cDNAs as templates.

Versican Expression

Four independent lines of versican-lacZ transgenic mice that showed easily detectable lacZ staining in their skin were obtained. The transgenic line A4681, which showed the strongest lacZ staining, was chosen for further detailed analysis, but similar expression patterns also obtained from the other lines as well. Intense lacZ staining was observed in developing fore and hind limbs at the E13.5 embryonic stage of the A4681 line in the region of mesenchymal condensation. This region coincides exactly with the area of prominent endogenous versican expression previously identified immunohistochemically (Kimata, K., Oike, Y., Tani, K., Shinomura, T., Yamagata, M., Uritani, M.& Suzuki, S. (1986) *J. Biol. Chem.* 261, 13517–13525). Transient expression in the ectoderm was also observed in limb regions, but was restricted to the tips of limbs. No skin epidermal expression was observed elsewhere in the body. In addition to the limb bud region, β-galactosidase histochemistry revealed lacZ-positive cells in the mesenchyme adjacent to the olfactory epithelium, and in the kidney glomeruli. The perichondrocytes surrounding cartilage, the fore- and hindbrain, facial mesenchyme, blood vessels, and muscle cells also exhibited lacZ staining. These expression patterns are consistent with previous observations of expression that were obtained using immunohistochemistry with versican-specific antibodies in rat (Bignami, A., Perides, G. & Rahemtulla, F. (1993) *J. Neurosci. Res.* 34, 97–106) and human (Bode-Lesniewska, B., Dours-Zimmermann, M. T., Odermatt, B. F., Briner, J., Heitz, P. U. & Zimmermann, D. R. (1996) *J. Histochem. Cytochem.* 44, 303–312). The in situ hybridization study showed that the localization of both lacZ and mouse versican mRNA expression were well correlated in kidney, olfactory epithelium, and vertebral cartilage for example. Sense control probes for lacZ showed only background signals. We conclude that the selected 839 bp of promoter sequence (−559 to +280) is sufficient to direct tissue-specific versican expression in vivo.

Versican Promoter Drives Condensed Mesenchymal-Specific Expression in Embryonic Transgenic Skin LacZ expression in developing skin was examined by X-gal histochemistry on sagittal sections of E13.5, E14.5, E15.5, and E17.5 transgenic mouse embryos. At E13.5, ectodermal staining was only observed in the hind and fore limbs. Occasional traces of lacZ staining were found in single mesenchymal cells, which may correlate with the earliest stage of condensation. Interestingly, at E14.5, condensed mesenchymal cells immediately beneath the ectodermal placodes were clearly lacZ positive, contrasting strongly with the surrounding negative mesenchymal cells. These positive sites numbered 4–5 per sagittal section of whole embryo. At E15.5, lacZ staining of condensed mesenchyme under hair plugs appeared more intense than at E14.5 and showed an increased number of lacZ-positive cells. By E17.5, the number and intensity of lacZ-positive cells were dramatically increased, yet still virtually restricted to the condensed mesenchyme located at the proximal tips of down-growing hair germs. Similar to the pelage follicle, the condensed mesenchyme of whisker follicles also exhibited lacZ staining at E13.5 and later.

The Versican promoter is active in the hair dermal papilla of transgenic skin during the anagen phase of the hair cycling LacZ staining was examined on skin sections from newborn transgenic mice through the second hair cycle. In the newborn, strong staining was confined to the DP cells of pre-formed hair follicles at the anagen (growth) phase. At this stage some diffuse staining was also observed in the dermis, especially in the upper dermis and surrounding hair follicles. In situ hybridization for the endogenous mouse versican probe revealed DP-specific mRNA expression at this stage). Interestingly, at mid to late anagen, transient epithelial lacZ staining was observed in the inner root sheath of the hair follicle. However, in the late anagen stage lacZ staining was again restricted entirely to DP cells. In the catagen (transitional phase) to telogen (resting phase) hair follicles, no lacZ staining was observed in club (resting) hair. Presumptive second germ DP showed trace lacZ staining. Strong DP-specific staining was again observed in the second anagen hair cycle phase. These lacZ expression patterns in embryonic skin show that versican promoter activity is associated with the growth phase of hair cycling.

Cell Sorting

Dissected skins from newborn versican-GFP transgenic mice (1–3 days old) were floated on a 0.25% trypsin solution (Gibco-BRL, Grand Island, N.Y.) for 16–20 hr at 4° C., after which time the epidermis was discarded. The separated dermis was minced and incubated with 0.25% collagenase for 1 hr at 37° C. with gentle stirring to dissociate cells. Microscopic observation revealed that this treatment dissociated most dermal cells, pre-formed follicles, and follicle-associated DP cells. Debris and remaining pre-formed follicles that were not dissociated were removed by passing the cell suspension through a 75 µm filter followed by low-speed centrifugation to avoid clogging the cell sorter. The resultant cell suspensions were mostly single cells, which allowed sorting for GFP-positive selection. Cell sorting was performed with a Moflo high-speed cell sorter (Cytomation, Ft. Collins, Colo.). GFP-positive and GFP-negative cells were pooled in collection tubes with 20% fetal calf serum solution. These isolated GFP-positive cells were defined as "sorted DP-derived cells".

Sorted GFP-positive Cell Culture

Sorted DP-derived cells were plated at $2 \times 10^6$ cells per 100 mm dish and cultured either in DMEM (Life Technologies) with 10% fetal calf serum or complete Chang's medium (Irvine Scientific, Santa Ana, Calif.). Cells were passaged every 4 days after trypsin treatment. Some cells were cultured on chamber slides (Nunc Inc., Naperville, Ill.) for microscopic observation. Fluorescent and phase-contrast images were taken by spot-cooled color digital camera (Diagnostic instruments Inc., Sterling Heights, Mich.) and merged images were created using the Adobe Photoshop software program.

RT-PCR

Total RNAs were prepared from approximately $5 \times 10^6$ sorted or cultured DP-derived cells in Trizol solution (Life Technologies, Grand Island, N.Y.), and first-strand cDNAs were synthesized using the Advantage RT-for-PCR Kit (Clontech). Semi-quantitative RT-PCR amplifications were performed using the following settings: 94° C. for 30 sec, 55° C. for 30 sec, 72° C. for 1 min; 25 cycles. The primers were specific to the sequences for mouse versican sequences (Ito, K., Shinomura, T., Zako, M., Ujita, M. & Kimata, K. (1995) *J. Biol. Chem.* 270, 958–965): 5'-GACGACTGTCT-TGGTGG-3', SEQ ID No.1 and 5'-ATATCCAAACAAGC-CTG-3', SEQ ID No.2 GFP: 5'-TGCAGTGCTTCAGC-CGCTAC-3', SEQ ID No.3 and 5'-CTCGTTGGGGTCTTTGCTCA-3', SEQ ID No.4 mouse GAPDH: 5'-TGAAGGTCGGAGTCAACGGA-3', SEQ ID No.5 and 5'-GATGGCATGGACTGTGGTCA-3' SEQ ID No.6.

Versican-GFP Transgenic Mouse

A second transgenic mouse line was generated, in which the same versican promoter fragment (−559 to +280) was fused with green fluorescent protein (GFP). The new transgenic line exhibited strong DP-specific GFP fluorescence in newborn skin in the same pattern as that seen in versican-lacZ transgenic mouse skin. Partially dissociated dermal cell suspensions further revealed that strong fluorescence originated from DP cells located at the bottom of pre-formed follicles. After complete dissociation of the dermis by collagenase, these follicle-associated GFP-positive DP cells were released into the cell suspension. Most of the pre-formed follicles that were found in the pellet had lost their fluorescent signal, indicating that the majority of the GFP-positive DP cells were released into the suspension. Cell suspensions were sorted according to GFP-positive and negative fluorescence (which should represent cells with either an active or inactive versican promoter) using a high-speed cell sorter. An intense GFP-fluorescent-cell sub-population (10–15% of the entire cell suspension) was observed in cells prepared from transgenic mice, while dermal cells from non-transgenic littermates showed no fluorescence. Post sorting analysis showed that sorted positive cells were approximately 98% pure. RT-PCR analysis showed an abundance of both GFP and versican mRNA in sorted GFP-positive cells relative to sorted negative cells, in which both GFP and versican mRNA were not detected. This confirms that versican promoter-driven GFP expression correlated with endogenous versican expression.

Loss of Versican Expression with Cell Passage

Most of the sorted GFP-positive cells survived in primary culture. These cultured GFP positives were spindle-shaped, small, aggregating, multi layer-forming cells with a short doubling time in Chang's medium (about 2 days) and a longer doubling time in DMEM+FCS medium (about 4 days). This morphology and behavior is consistent with that of human scalp DP cells reported previously (Warren, R., Chestnut, M. H., Wong, T. K., Otte, T. E., Lammers, K. M. & Meili, M. L. (1992) *J. Invest. Dermatol.* 98, 693–699). However, even after the first passage (4 days), the relative number of GFP-fluorescent cells was significantly decreased, with approximately less than 20% of the initial GFP-positive cells remaining. This loss coincided with a decrease in versican mRNA.

Induction of Hair Growth in vivo

The method for inducing hair growth in vivo was performed as described previously, except that 3T3 fibroblast cells were not added since they showed no significant contribution to hair inductivity in initial experiments (Kamimura, J., Lee, D., Baden, H. P., Brissette, J. & Dotto, G. P. (1997) *J. Invest. Dermatol.* 109, 534–540). Epithelial cells (keratinocytes) were freshly prepared from either newborn CD-1 or C3H strain mouse skins by trypsin treatment and release from epidermal sheets by gentle stirring. Either sorted GFP-positive cell suspension ($5 \times 10^6$), sorted negative cell suspension ($5 \times 10^6$), or unsorted cell suspension ($1 \times 10^7$) was combined with keratinocytes ($4 \times 10^6$), resuspended in 100 µl medium, and transferred to a grafting chamber, which was implanted onto the dorsal skin of nude mice (nu/nu). Sorted positive cells without epithelial cells were also grafted. The chamber was removed after 1 week, and hair formation was assessed 3 weeks later and thereafter. For histological observation grafting sites were dissected 3 weeks after the graft. For the grafting using cultured cells, the cultured GFP-positive cells were harvested with trypsin after first passage (4 days) and re-sorted for GFP positive and negative selection. The same number of resorted GFP-positive and negative cultured cells ($5 \times 10^6$), were grafted with keratinocytes. All animal procedures had the approval of the Massachusetts General Hospital Animal Care and Use Committee.

Versican Expression Coincided with in vivo Dermal Condensation and Hair Inductive Ability To examine whether versican expression correlates with hair inductive ability, freshly sorted DP-derived cells mixed with keratinocytes were grafted to the back skin of nude mice. Only GFP-positive cells resulted in newly formed hair; sorted negative cells did not (Table 1).

TABLE 1

Hair-Forming Potency of GFP-Positive and Negative Cells by an In Vivo Cell Grafting Assay

| Dermal component | Epidermal component | Success rate |
| --- | --- | --- |
| sorted GFP + cells | keratinocytes | 7/7 (4) 100% |
| sorted GFP − cells | keratinocytes | 0/5 (3) 0% |
| sorted GFP + cells | None | 0/3 (2) 0% |
| unsorted dermal cells | keratinocytes | 3/3 (2) 100% |
| re-sorted GFP + cultured cells | keratinocytes | 3/3 (2) 100% |
| re-sorted GFP − cultured cells | keratinocytes | 0/4 (2) 0% |

Number of haired mice/number of mice grafted; numbers in parentheses are the number of experiments performed separately.

Full development of hair shaft elongation was maintained for 4 months after grafting. Sorted GFP-positive cells that were cultured for 4 days, where most cells had lost the fluorescent signal, were resorted. The resorted GFP-positive subpopulation was also able to induce hair formation while GFP-negative cultured cells from a second sorting did not (Table 1), confirming that versican expression correlated with hair inductive ability. Histologic sections after three weeks from sites where the GFP-positive cells were grafted with keratinocytes clearly showed GFP-positive fluorescence within the condensed DP. Grafting with GFP-positive sorted cells alone in the absence of epithelial cells did not result in hair formation (Table 1). Sections from these grafting sites exhibited diffuse GFP fluorescence in the upper dermis but no sign of condensation. Thus, the epidermal component is required for dermal condensation and hair induction. GFP fluorescence was observed in condensed DP cells in the tissue weeks after grafting, implying that the loss of GFP fluorescence in culture on passage reflects the loss of versican promoter activity, rather than merely the fading of GFP protein.

Our results demonstrate that continuous expression of versican is required for the aggregating property of DP cells. In addition, we observed no lacZ-positive 'free' fibroblasts in the surrounding dermis close to the already condensed mesenchymal cells. This suggests that dermal condensation results from the proliferation of a small number (possibly even one) of mesenchyme cells that first associate with the epithelial placode.

Continuous versican expression in condensed mesenchymal cells is required to exclude additional surrounding dermal fibroblasts from the condensation, maintaining the purity of the induced DP cell population. Although the versican immunoreactivity was not detected in early embryonic mouse (du Cros, D. L., LeBaron, R. G. & Couchman, J. R. (1995) *J. Invest. Dermatol.* 105, 426–431), this may be due to the higher sensitivity of the histochemical detection of lacZ based upon the β-galactosidase enzymatic reaction.

In any case, this property of the versican promoter is useful for targeting condensed mesenchyme-specific gene expression, e.g., in the study of epithelial-mesenchymal interactions in general as well as in the study of hair development. Because the 280 bp of 5' untranslated region after the transcriptional initiation site exhibits the condensing mesenchyme-specific expression, response elements for DP-specific expression may be confined to the remaining 559 bp of the promoter sequence. Cursory examination of the sequence reveals potential AP-2 (Naso, M. F., Zimmermann, D. R. & Iozzo, R. V. (1994) *J. Biol. Chem.* 269, 32999–33008), LEF-1 (Zhou, P., Byrne, C., Jacobs, J. & Fuchs, E. (1995) *Genes & Dev.* 9, 700–713), and Pax (Dahl, E., Koseki, H. & Balling, R. (1997) *Bioessays* 19, 755–765) transcription factor-binding sequences.

Passaging DP-derived primary cell cultures rapidly turned off versican expression. Previous reports showed that cultured dermal cells passaged from primary to four times failed to support hair growth in a cell grafting assay (Weinberg, W. C., Goodman, L. V., George, C., Morgan, D. L., Ledbetter, S., Yuspa, S. H. & Lichti, U. (1993) *J. Invest. Dermatol.* 100, 229–236). The present data showed that versican-expressing DP cells have hair inductivity even after primary culture, if versican-positive cells are concentrated by resorting. This could suggest that there is an insufficient number of versican-expressing DP cells in ordinary dermal culture. Alternatively, the cell densities of the primary cell cultures may affect the versican expression and hair inductivity of DP cells.

We believe that DP cells require a factor(s) originating from epithelial cells for versican expression, and possibly for hair inductive ability. This is supported by the fact that dermal condensation and hair formation occurred only when epithelial cells were grafted with concentrated DP cells. Using these sorted DP-derived cells (with GFP as a reporter) to search for the condition or factors that stimulate versican expression could lead to detection of an essential signaling molecule(s).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
providing a cultured skin mesenchymal cell that comprises a human versican promoter;
providing a test compound or a test condition to the cultured skin mesenchymal cell;
evaluating versican promoter activity in the cultured skin mesenchymal cell; and
monitoring hair growth or induction of hair growth in the presence of the test compound or the test condition, wherein the method includes the step of implanting the skin mesenchymal cell in an animal.

2. The method of claim 1, wherein the skin mesenchymal cell is a dermal papilla (DP) cell.

3. A method comprising:
providing a cultured versican-expressing human skin mesenchymal cell;
providing a test compound or a test condition to the cultured skin mesenchymal cell;
evaluating versican gene expression in the cultured skin mesenchymal cell; and
monitoring hair growth or induction of hair growth in the presence of the test compound or the test condition, wherein the method includes the step of implanting the skin mesenchymal cell in an animal.

4. The method of claim 3 wherein the skin mesenchymal cell is a dermal papilla (DP) cell.

5. The method of claim 1 or 3 wherein the step of providing the test compound or the test condition occurs in the presence of epithelial cells or an extract thereof.

6. The method of claim 5 wherein the epithelial cells are epithelial hair germ cells.

7. The method of claim 5 wherein the epithelial cells are placode cells.

8. The method of claim 1 or 3 wherein hair growth is monitored.

9. The method of claim 1 or 3 wherein hair induction is monitored.

10. The method of claim 1 or 3 wherein the skin mesenchymal cell is provided with the test condition.

11. The method of claim 10 wherein the test condition comprises heat-shock, freezing or laser treatment.

12. The method of claim 1 or 3 wherein the skin mesenchymal cell is provided with the test compound.

13. The method of claim 12 wherein the test compound is a polypeptide or polynucleotide.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: oligonucleotide for PCR

<400> SEQUENCE: 1
gacgactgtc ttggtgg                                                  17

<210> SEQ ID NO 2
<211> LENGTH: 17
<212> TYPE: DNA
<213> ORGANISM: Artificial Sequence
<220> FEATURE:
<223> OTHER INFORMATION: oligonucleotide for PCR

<400> SEQUENCE: 2
atatccaaac aagcctg                                                  17

<210> SEQ ID NO 3
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 3
tgcagtgctt cagccgctac                                               20

<210> SEQ ID NO 4
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 4
ctcgttgggg tctttgctca                                               20

<210> SEQ ID NO 5
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 5
tgaaggtcgg agtcaacgga                                               20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide for PCR

<400> SEQUENCE: 6
gatggcatgg actgtggtca                                               20